United States Patent [19]

Van Leverink

[11] 4,280,997

[45] Jul. 28, 1981

[54] EXTRUSION PROCESS FOR THE PREPARATION OF ANHYDROUS STABLE LACTOSE

[76] Inventor: Johannes Van Leverink, Grevelingenhof 3, Veghel, Netherlands

[21] Appl. No.: 100,872

[22] Filed: Dec. 6, 1979

[30] Foreign Application Priority Data

Dec. 8, 1978 [NL] Netherlands .......................... 7812002

[51] Int. Cl.³ ........................ C13K 5/00; A61K 33/16
[52] U.S. Cl. ..................................... 424/151; 127/31; 127/42; 127/63; 536/1
[58] Field of Search ............................ 127/31, 42, 63; 424/151; 536/1

[56] References Cited

U.S. PATENT DOCUMENTS

| | | | |
|---|---|---|---|
| 2,182,619 | 12/1939 | Sharp | 127/31 |
| 2,319,562 | 5/1943 | Sharp | 127/31 |
| 3,802,914 | 4/1974 | Nezbed | 127/61 |
| 4,083,733 | 4/1978 | Asano | 127/31 X |

FOREIGN PATENT DOCUMENTS 2115116 10/1971 Fed. Rep. of Germany .
1667038 4/1972 Fed. Rep. of Germany .
7613257 5/1978 Netherlands .

OTHER PUBLICATIONS

Chemical Abstracts, 65:8681c (1966).

*Primary Examiner*—Sidney Marantz

[57] ABSTRACT

Anhydrous stable lactose is obtained by extruding crystalline α-lactose hydrate as a dry product in an extruder the jacket of which is heated to temperatures above 100° C. Preferably an extruder is used in which a gradual controlled build-up of shear takes place.

6 Claims, 2 Drawing Figures

EXTRUSION PROCESS FOR THE PREPARATION OF ANHYDROUS STABLE LACTOSE

Usually lactose is obtained on an industrial scale by cooling a supersaturated solution of lactose at temperatures below 93° C. and separating and drying the resulting solid substance. The resulting lactose is obtained in the form of α-lactose hydrate containing 1 molecule of hydrate water per molecule of lactose, which means about 5 percent by weight of hydrate water.

An important field for the use of lactose is the pharmaceutical industry, where the lactose is used when manufacturing tablets and capsules. However, it is generally known that the presence of moisture in any form in tablets and capsules may have a negative influence upon the quality of these tablets or capsules, for example because the water reacts with the active ingredient in the tablet or the capsule. Thus the use of α-lactose hydrate may encounter difficulties. Moreover, strong tablets can only be formed with difficulty with the usual α-lactose hydrate crystals. Therefore, normally binders and/or lubricants and optionally water are added to the lactose, whereafter by tabletting in the conventional way sufficiently strong tablets can be manufactured (cf. for example German patent application No. 2,115,116). It is also known from the German patent application No. 1,667,038 to knead lactose powder with 20 percent by weight of water, to extrude the kneaded product to form granules and to subject these granules in a special way to centrifugal forces in an apparatus with rotating disks.

From Chemical Abstracts, 65 (1966), 8681 c it is known that anhydrous lactose is very suitable as a diluent in tablets.

As such it is already known to prepare anhydrous lactose from α-lactose hydrate. According to the U.S. Pat. No. 2,319,562 α-lactose hydrate is heated to a temperature, which is sufficiently high to set free the water of crystallization. However, the heated crystals must be present in a water vapour environment having a carefully controlled water vapour pressure. If the water vapour pressure is low, an unstable form of the anhydrous α-lactose is obtained. If the water vapour pressure is high, β-lactose is formed. The heating can be carried out in various manners, e.g. in an autoclave, in a rotary kiln, on a heated dish, in an organic solvent or on a roll drum drier.

According to the U.S. Pat. No. 3,802,914 an aqueous lactose solution containing from 40 to 60 percent by weight of lactose is sprayed onto a heated surface. Thus, a lactose product is obtained containing at least 50 percent by weight of amorphous lactose, at least 65 percent by weight of β-lactose and at least 20 percent by weight of crystalline β-lactose. Preferably, the heated surface is a rotating drum. Disadvantages of this process are that an aqueous lactose solution instead of dry lactose is used as a starting material, so that an additional evaporation of water is necessary, that drum drying of a solution having a low viscosity gives rise to leakages, so that losses occur, and that the product is obtained as a film and after milling shows insufficient free-flowing properties in connection with the film structure. However, it is known that good free-flowing properties are very important for manufacturing strong tablets and capsules.

From the Netherlands patent application No. 7613257 a process for the preparation of β-lactose is known, which comprises adding to α-lactose or an α-lactose containing material a small amount of water, e.g. 1.5 to 15 percent by weight, based on the starting material, and extruding the resulting mixture in a conventional extruder under a pressure of preferably 5 to 40 kg/cm$^2$ at a temperature of preferably 100° to 200° C., whereby α-lactose is converted into β-lactose. It has been stated in this patent application that the use of the process is impossible when too small an amount of water is added.

It has now been found that anhydrous stable lactose having a specific physical structure can be obtained when crystalline α-lactose hydrate is introduced as a dry product into an extruder, the jacket of which is heated to temperatures above 100° C. At these temperatures above 100° C. the α-lactose hydrate is heated under pressure, whereafter it is extruded. Immediately thereafter evaporation of water takes place. The resulting product has a dry solids content of more than 99 percent by weight.

Figure 1:
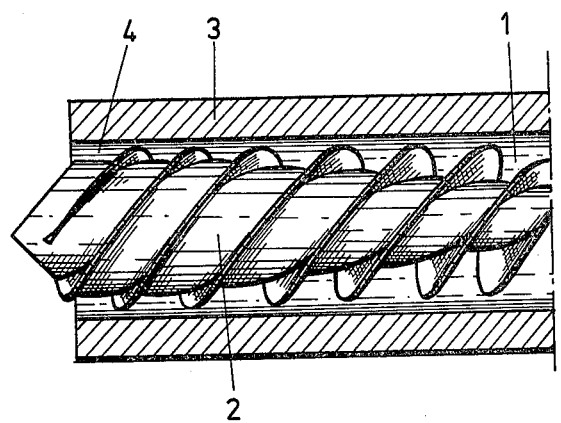
FIG. 1 depicts an extruder providing for the gradual controlled build-up of shear of the instant invention.
Figure 2:
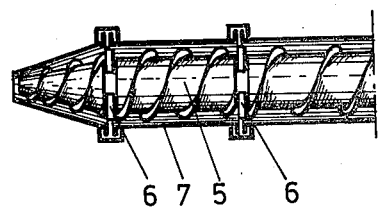
FIG. 2 depicts a conventional extruder for comparison.

It has further been found that the extrusion of the dry α-lactose hydrate can only take place with a satisfactory result, if an extruder is used of a type in which a gradual controlled build-up of shear takes place. Extruders of this type are for example extruders of the so-called Battenfeld-design, in which the diameter of the worm shaft first increases conically, whereafter a cylindrical portion follows, as shown in FIG. 1 and explained in more detail in example 1. However, also other extruders with a single worm shaft or with double worm shafts are useful in the process of the invention provided therein a gradual, controlled build-up of shear takes place. This means that abrupt variations in the build-up of shear must be avoided. Such abrupt variations occur for example, when the cross-section of the space between worm shaft and jacket of the extruder is subject to sudden changes. Thus, extruders of the type, which is often used in the preparation of foodstuffs (extrusion cooking) as shown in FIG. 2 and explained in more detail in example 2, appeared to be not suitable in the process of the invention. In these extruders the build-up of shear does not take place gradually, because the annular space between worm shaft and jacket, through which the lactose mass is pressed, is narrowed at one or more places over a very short distance by increase of the diameter of the worm shaft.

Using an extruder of the last-mentioned type a mixture of α-lactose hydrate and water may be extruded according to the process described in the Netherlands patent application No. 7613257, provided at least 1.5 percent by weight, but preferably more than 4 percent by weight of water are added. However, by this process a product is obtained, which after cooling contains 1 percent by weight of water or more and therefore must be dried in a separate step, before it can be considered as anhydrous. Such after-dried products often show unacceptable hygroscopic properties, possibly as a result of the presence of unstable or amorphous forms of lactose. Because in the process of the invention water is not added, an anhydrous product can be obtained without after-drying, the hydrate water being evaporated from the extruded product immediately after this has left the extruder. For that purpose the hot extrusion product is preferably cooled with the aid of dry air.

By a proper selection of the shape of the orifice of the extruder the extruded product may be obtained as a filament or a rod. By variation of the conditions and of the shape of the orifice the product may also be extruded as a ribbon or in another shape. Also the diameters of the extruded products may be varied.

Optionally the resulting filament, rod or ribbon can be comminuted by means of a rotating knife to obtain granules the size of which can be adjusted as desired. It is also possible to mill the resulting extruded product and to obtain the desired particle size by a proper selection of the milling intensity.

All above mentioned methods of shaping, comminuting and milling the extruded products are generally known in the art.

It has appeared that on an excenter press tablets may be manufactured with the milled anhydrous product with the addition of 0.5 percent by weight of a lubricant. The resulting tablets resist a pressure of 10–13 kg.

When carrying out the process of the invention it is also possible to extrude other substances, such as anhydrous lactose or certain substances with a pharmacological action, together with the α-lactose hydrate. In this way a product may be obtained, for example, in which a small amount of pharmacologically active substance is distributed homogeneously in the carrier of anhydrous stable lactose and may be pressed therewith immediately to form tablets. In this way sodium fluoride may be dispersed in lactose.

With the anhydrous lactose prepared according to the invention also stable capsules may be prepared.

The following examples serve to illustrate the invention without restricting it.

EXAMPLE I (According to the invention.)

Crystalline α-lactose hydrate was extruded in an extruder of the so-called Battenfeld-design having a conical-cylindrical worm shaft, as shown in FIG. 1. In the space between the conical portion (1) of the worm shaft (2) and the jacket (3) of the extruder the product to be extruded is subjected to an increasing shear in a gradual way which is controlled by the shape of the worm shaft and the jacket. Thereafter the product is pressed through the space between the cylindrical portion (4) of the worm shaft and the jacket, where shear remains constant. The jacket was heated at 162° C. In a period of two hours 26 kg of anhydrous lactose having a moisture content of less than 0.3% by weight were prepared. The product was not hygroscopic and contained 82.8% by weight of β-lactose.

EXAMPLE II (For comparative purposes.)

Crystalline α-lactose hydrate was introduced into an extruder comparable with the extruder used in the process of the Netherlands patent application No. 7613257, as shown in FIG. 2. The cylindrical worm shaft (5) is enlarged at two places by abrupt annular enlargements (6), indicated as steamlocks. In the space between these steamlocks and the jacket (7) the product is suddenly and in an uncontrolled way subjected to a strong shear.

The jacket was heated at 164° C. It appeared impossible to process the α-lactose hydrate in a dry state with this extruder. However, when 4% by weight of water or more was added to the α-lactose hydrate, the mixture could be extruded without difficulties. As soon as the addition of water was stopped, however, the extrusion process was interrupted and no further extruded product was obtained.

I claim:

1. A process for the preparation of anhydrous stable lactose, comprising introducing crystalline alpha-lactose hydrate as a dry product into an extruder, wherein a gradual, controlled, build-up of shear takes place and wherein the jacket of said extruder is heated to temperature above 100° C. such that anhydrous stable lactose is produced, and extruding said crystalline alpha-lactose with this extruder.

2. The process of claim 1, wherein the heating of said crystalline alpha-lactose hydrate liberates water of hydration and said water is evaporated from the extruded product immediately after it has left the extruder.

3. The process of claims 1 or 2, wherein said alpha-lactose hydrate is introduced into said extruder in admixture with anhydrous lactose or a small amount of a pharmacologically active substance.

4. The process of claims 1 or 2, wherein the extruded product is formed in a selected shape and/or size.

5. A process for manufacturing tablets containing anhydrous stable lactose, wherein said anhydrous lactose is prepared according to the process of claims 1 or 2, said process comprising pressing said anhydrous lactose to form said tablet.

6. A process for manufacturing capsules containing anhydrous stable lactose wherein said lactose is prepared according to the process of claims 1 or 2, said process comprising adding said lactose to a suitable container to form a capsule.

* * * * *

UNITED STATES PATENT AND TRADEMARK OFFICE
CERTIFICATE OF CORRECTION

PATENT NO. : 4,280,997
DATED : July 28, 1981
INVENTOR(S) : Johannes van Leverink It is certified that error appears in the above—identified patent and that said Letters Patent is hereby corrected as shown below:

On the cover sheet Insert:

-- Assignee: (73) DMV-Campina B.V., Veghel, Netherland --.

Signed and Sealed this

Twenty-second Day of December 1981

[SEAL]

Attest:

GERALD J. MOSSINGHOFF

Attesting Officer

Commissioner of Patents and Trademarks